US006759430B2

(12) United States Patent
Anggard et al.

(10) Patent No.: US 6,759,430 B2
(45) Date of Patent: *Jul. 6, 2004

(54) PIPERIDINE AND PYRROLIDINE DERIVATIVES COMPRISING A NITRIC OXIDE DONOR FOR TREATING STRESS

(75) Inventors: Erik Emil Anggard, Marsh Baldon (GB); Abdullah Ibrahim Haj-Yehia, Jerusalem (IL)

(73) Assignee: OxoN Medica Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/205,997

(22) Filed: Jul. 25, 2002

(65) Prior Publication Data

US 2003/0069429 A1 Apr. 10, 2003

Related U.S. Application Data

(63) Continuation of application No. 09/600,711, filed as application No. PCT/GB99/00231 on Jan. 22, 1999, now Pat. No. 6,448,267.

(30) Foreign Application Priority Data

Jan. 22, 1998 (GB) .............................. 9801398

(51) Int. Cl.[7] ..................... A61K 31/40; A61K 31/445; C07D 207/46; C07D 207/12; C07D 207/08
(52) U.S. Cl. ..................... 514/425; 514/423; 514/424; 514/315; 514/316; 514/212.01; 548/537; 548/542; 548/531; 548/565; 546/188; 546/216; 546/219; 546/242; 540/604
(58) Field of Search ................. 548/537, 542, 548/531, 565; 514/423, 424, 425

(56) References Cited

U.S. PATENT DOCUMENTS

| 4,845,090 A | * | 7/1989 | Gries et al. ................. 424/9.33 |
|---|---|---|---|
| 5,352,442 A | | 10/1994 | Proctor |
| 5,621,000 A | | 4/1997 | Arena et al. |
| 5,700,947 A | | 12/1997 | Soldato |
| 5,780,495 A | | 7/1998 | Del Soldato |
| 5,824,669 A | | 10/1998 | Garvey et al. |
| 5,861,426 A | | 1/1999 | Del Soldato et al. |
| 5,977,090 A | | 11/1999 | Slusher et al. |
| 6,040,341 A | | 3/2000 | Del Soldato et al. |
| 6,043,252 A | | 3/2000 | Bombrun |
| 6,143,746 A | | 11/2000 | Daugan et al. |
| 6,197,762 B1 | | 3/2001 | Garvey et al. |
| 6,211,233 B1 | | 4/2001 | Del Soldato |
| 6,232,331 B1 | | 5/2001 | Sankaranarayanan |
| 6,242,432 B1 | | 6/2001 | del Soldato |
| 6,248,895 B1 | | 6/2001 | Sankaranarayanan |

FOREIGN PATENT DOCUMENTS

| AU | 733202 | 10/1997 |
|---|---|---|
| EP | 0 135 316 | 3/1985 |
| GB | 1 315 524 | 5/1973 |
| GB | 2349385 | 11/2000 |
| JP | 02099323 A2 * | 4/1999 |
| WO | WO 95/30641 A1 | 11/1995 |
| WO | WO 96/32946 A1 | 10/1996 |
| WO | WO 96/39409 A1 | 12/1996 |
| WO | WO 97/31654 A1 | 9/1997 |
| WO | WO 97/33609 A1 | 9/1997 |
| WO | WO 98/20336 A1 | 5/1998 |
| WO | WO 98/42661 | 10/1998 |
| WO | WO 98/55453 A1 | 12/1998 |
| WO | WO 99/40787 A1 | 8/1999 |
| WO | WO 99/61018 A1 | 12/1999 |
| WO | WO 99/61430 A1 | 12/1999 |
| WO | WO 99/66918 A1 | 12/1999 |
| WO | WO 99/66924 A1 | 12/1999 |
| WO | WO 00/15228 A1 | 3/2000 |
| WO | WO 00/15639 A1 | 3/2000 |
| WO | WO 00/31060 A1 | 6/2000 |
| WO | WO 00/35434 A2 A3 | 6/2000 |
| WO | WO 00/67754 A1 | 11/2000 |
| WO | WO 01/08684 A1 | 2/2001 |
| WO | WO 01/32202 A1 | 5/2001 |

OTHER PUBLICATIONS

Jia et al. (1993). "Inhibition by Sulfhydryl Compounds of Vascular Relaxation Induced by Nitric Oxide and Endothelium–Derived Relaxing Factor," *J. Pharm. & Experimental Therapeutics* 267(1):371–378.

Kirilyuk et al. (1991). "Synthesis of 2H–Imidazole 1–Oxides and Their Corresponding Stable Nitroxide Radicals," *Chem. Ab.*116:20993 & *Izv. Akak. Nauk. SSSR. Ser. Khim* 9:2113–2122.

Kowaluk et al. (1990). "Spontaneous Liberation of Nitric Oxide Cannot Account for In Vitro Vascular Relaxation by S–Nitrosothiols," *J. Pharm. & Experimental Therapeutics* 255(3):1256–1264.

Münzel et al. (1995). "Evidence for Enhanced Vascular Superoxide Anion Production in Nitrate Tolerance," *J. Clin. Invest., Inc.* 95:187–194.

Robak et al. (1993). "Nitride Oxide Donors as Generators and Scavengers of Superoxide Anions," *Chem. Ab.* 119:262465 & *Pol. J. Pharmacol.*45(1):51–58.

(List continued on next page.)

*Primary Examiner*—Evelyn Mei Huang
(74) *Attorney, Agent, or Firm*—Morrison & Foerster LLP

(57) ABSTRACT

The present invention relates to chemical compounds comprising a nitric oxide (NO) donor and a superoxide ion ($O_2^-$) scavenger, their preparation and their use in the treatment of conditions associated with oxidative stress or endothelial dysfunction. In particular, the present invention relates to chemical compounds of Formula (I) wherein: $R^1$ may be the same of different and are independently selected from hydrogen, alkoyl, carboxy, hydroxy, amino, amido, cyano, nitro, thio, sulphonyl, sulphoxide alkyl groups comprising an NO-donor, provided that at least one $R^1$ is a group comprising an NO-donor; $R^2$ may be the same or different and are independently selected from alkyl groups; n is an integer 1, 2, or 3; or a salt thereof.

42 Claims, 8 Drawing Sheets

OTHER PUBLICATIONS

Sen, V.D. (1996). "Synthesis and Antitumour Activity of Platinum (II) Complexes with trans–3,4–diamino–2,2,6, 5–tetramethylpiperidine–1–oxyl," *Chem. Ab.* 125:315130 & *J. Inorg. Biochem.*64(1):69–77.

Singh et al. (1984). *Acta Chim. Hung.* 115(1):3–7.

Ziyatdinov et al. (1991). "Anomolous Nitration of 1–fluoro–, and 1–bromo–2propene with Dinitrogen Trioxide," *Chem. Ab.* 116:150921 & *Izv. Vyssh. Uchebn. Zaved. Khim. Khim. Tekhnol.* 34(11):37–44.

Ziyatdinov et al. (1993). "Nitration of Unsaturated Compounds. 5. Mechanism of Reaction of Allyl Chloride with Dinitrogen Tetroxide," *Chem. Ab.* 120:190738 & *Izv. Vyssh. Uchebn. Zaved. Khim. Khim. Tekhnol.* 36(7):22–28.

Krishna et al. (1998). "Studies of Structure–Activity Relationship of Nitroxide Free Radicals and Their Precursors as Modifiers Against Oxidative Damage," *J. Med. Chem.* 41:3477–3492.

Tat'yanenko et al. (1996). "Bioantioxidants as Inhibitors of Aldehyde Reductase," *Pharm. Chem. J.* 30(6):361–362.

* cited by examiner

PIPERIDINE AND PYRROLIDINE DERIVATIVES COMPRISING A NITRIC OXIDE DONOR FOR TREATING STRESS

CROSS-REFERENCE TO RELATED APPLICATIONS

This application is a continuation of U.S. application Ser. No. 09/600,711, filed Sep. 5, 2000, now U.S. Pat. No. 6,448,267 which is a 371 of PCT/GB99/00231, filed on Jan. 22, 1999, which claims the benefit of United Kingdom 9801398.0, filed Jan. 22, 1998, the disclosures of each of which are incorporated herein by reference in their entirety.

The present invention relates to compounds capable of acting both as sources of nitric oxide (NO-donors) and as scavengers of superoxide ion ($O_2^-$) (superoxide dismutase (SOD)-mimetic).

Many disease states, including diabetes mellitus and various cardiovascular diseases, are associated with oxidative stress and endothelial dysfunction. In particular, endothelial dysfunction is the hallmark of the pathophysiological process (atherosclerosis) leading to a spectrum of clinically related diseases of the cardiovascular system (e.g. from stable angina pectoris to myocardial infarction (MI) and congestive heart failure), as well as being the primary event in pathologies relating to other body systems involving superoxide and/or other reactive oxygen species (ROS).

For over a century, nitroglycerin (GTN) has been the drug of choice for the treatment of various types of myocardial ischemia (angina), including myocardial infarction, and a mainstay in the treatment of other heart diseases with and without ischemic etiology (congestive heart failure, isolated systolic and resistant hypertension). Because of its pathogenic nature (chronicity with acute exacerbation), prophylactic and acute treatments are necessary to prevent complications with potentially fatal outcomes (>25% death for acute MI).

However, the phenomenon of tolerance to the anti-anginal effects of GTN and to all other existing organic nitrates is of a special clinical significance. In particular, early development of tolerance to the drug is by far the most serious drawback of nitrate therapy, especially during acute myocardial infarction.

Evidence has been provided to support an involvement of the superoxide anion in the mechanism/s underlying nitrate tolerance and cross-tolerance (Munzel et al., J. Clin. Invest. 95, 187–194 (1995)). According to this report, increased levels of superoxide anion were found to accompany tolerance development to GTN in vascular tissue after in vivo administration of the drug. Treatment with superoxide dismutase (SOD) significantly enhanced maximal relaxation of control and tolerant vascular tissue to GTN and other exogenous and endogenous vasodilators. This can be explained on the basis of an enhancing effect of superoxide on the induction of tolerance (pseudo-tolerance). It is believed that if the normally tightly controlled balance between nitric oxide (NO) and superoxide ($O_2^-$) in the vascular wall is disturbed, elevated levels of superoxide anion prevail, inactivating NO and furthermore generating toxic peroxynitrite. The protective effect of superoxide dismutase against nitrate tolerance has been demonstrated in vitro (Jia et al., J. Pharmacol. Exp. Ther., 267,371-378 (1993) and Kowaluk et al., J. Pharmacol. Exp. Ther., 255, 109–144 (1990)). However, being an enzyme, SOD is practically cell impermeable and cannot therefore be used therapeutically. There remains therefore a need for a nitrate-based therapy which does not suffer from the problem of nitrate tolerance.

According to the present invention there is provided a chemical compound comprising a nitric oxide (NO) donor and a superoxide ($O_2^-$) scavenger.

The nitric oxide donor may comprise any group capable of acting as a source of nitric oxide (NO). Preferably, the nitric oxide donor is an —$ONO_2$ group. The superoxide scavenger may comprise any group capable of acting as a scavenger of superoxide ($O_2^-$). Preferably, the superoxide scavenger is a nitroxide free radical (N→O.) group.

The compounds of the present invention may comprise one or more NO donors and one or more superoxide scavengers.

The compounds of the present invention not only provide a source of nitric oxide but in acting as an antioxidant scavenger of superoxide anion give rise to both a direct benefit derived from removal of injurious superoxide anion and a benefit in protecting both ambient and endogenous and liberated exogenous NO from inactivation by superoxide anion.

Without prejudice to the scope of the present invention, it is believed that oxidative damage is mediated by intracellular redox-active metal reactions catalyzed by highly reactive oxygen species (i.e. hydroxyl radicals). The generation of such reactive oxygen products depends on the availability of their common precursor, the superoxide anion. Mitochondria, microsomes and other various enzyme systems are known to produce superoxide anion that reacts with nitric oxide at or near diffusion controlled rates to form the powerful oxidant peroxynitrite. At pH 7.4, peroxynitrite protonates to form peroxynitrous acid (pKa 6.6) which decays homolytically to form hydroxyl and nitrogen dioxide radicals in addition to a host of other ions. The extent to which these later reactive ions and radicals can cause cellular damage and death depends on the rate of formation of their peroxynitrite precursor. Under control (non-diseased) conditions, where the levels of NO are found in equilibrium between rates of NO-synthesis and degradation, the rate of formation of this peroxynitrite precursor is thought to depend solely on the levels of the superoxide anion. This is particularly important in cases involving "below-normal" levels of "biologically active" NO, such as in diseases for which therapeutic intervention with exogenous NO-donors is clinically indicated. Consequently, the extra- and intra-cellular activity of the enzyme SOD must have a cardinal role in maintaining cellular survival, tissue integrity and adequately balanced physiological function.

Since superoxide anion is an available and continuously-formed by-product generated through normal metabolic processes, and since its elimination is mediated either by dismutation by the enzyme SOD or via its reaction with NO to form the potentially hazardous peroxynitrite, it is now believed that the ultimate means by which a modification and/or treatment of 'pathological processes' involving imbalanced ratio of NO to superoxide is by an intervention with therapeutic agents capable of simultaneously and favourably affecting both components; the NO and $O_2^-$.

By virtue of the NO donor and superoxide scavenging activities being physically linked in the same molecule, the compounds of the present invention ensure that an increase in the level of NO is accompanied by reduced levels of superoxide thereby avoiding high levels of peroxynitrite and oxidant metabolites thereof. Preferred compounds according to the present invention are of the formula:

Preferred compounds according to the present invention are of the formula:

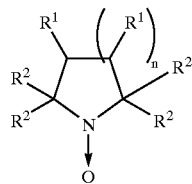

wherein R¹ may be the same or different and are independently selected from hydrogen, alkoyl, alkoxy, carboxy, hydroxy, amino, amido, cyano, nitro, thio, sulphonyl, sulphoxide, alkyl groups and groups comprising an NO-donor, provided that at least one R¹ is a group comprising an NO-donor group;

R² may the same or different and are independently selected from alkyl groups;

n is an integer 1, 2 or 3;
or a salt thereof.

The groups R¹ may be the same or different and are independently selected from hydrogen, alkoyl, alkoxy, carboxy, hydroxy, amino, amido, cyano, nitro, thio, sulphonyl, sulphoxide, alkyl groups and groups comprising an NO-donor group, provided that at least one R¹ is a group comprising an NO-donor. R¹ groups which do not comprise an NO-donor group are preferably hydrogen or alkyl groups. Each R¹ group comprising an NO-donor group may comprise one or more NO-donor groups. Preferably, each NO-donor group is an —ONO₂ group.

Each R¹ group comprising an NO-donor group may comprise an NO-donor group alone or may comprise an NO-donor group linked via a C₁ to C₂₀ alkylene chain optionally comprising one or more heteroatoms. The alkylene chain may be branched or unbranched, cyclic or acyclic, saturated or unsaturated, where cyclic the alkylene chain is preferably C₃ to C₁₂, more preferably C₅ to C₁₀, more preferably C₅ to C₇. Where acyclic, the alkylene chain is preferably C₁ to C₁₆, more preferably C₁ to C₆. The alkylene chain may be unsubstituted or substituted as defined hereinbelow in respect of alkyl groups. The alkylene chain may comprise one or more heteroatoms, for example nitrogen, oxygen or sulphur atoms which may interrupt the alkylene chain or may link the alkylene chain to the NO-donor group or to the rest of the molecule (such that the R¹ group comprising the NO-donor group is linked to the rest of the molecule via a heteroatom, such as an oxygen (e.g. ether linkage), nitrogen (e.g. amino or amido linkage) or sulphur (e.g. thioether linkage)).

Preferred R¹ groups comprising NO-donors comprise groups of the formula:

—X—Y—ONO₂ where X is absent or is O, NH or S; and

Y is a C₁₋₂₀ alkylene chain

Preferably, X is O, NH or S.

In a preferred embodiment, at least one R¹ is a polar or ionisable group such as carboxyl or amino, which improves the solubility of the compound.

The groups R² may be the same or different and are selected from alkyl groups. Preferably, the groups R² are each methyl groups. In an alternative preferred embodiment, one or more of the groups R² is a lipophilic group, such as a substituted or unsubstituted C₁ to C₈ alkyl group, capable of assisting in transport of the compound across the blood-brain membrane.

n may be 1, 2 or 3. Preferably n is 1 or 2, More preferably n is 2.

As used here reference to alkyl groups means a branched or unbranched, cyclic or acyclic, saturated or unsaturated (e.g. alkenyl or alkynyl) hydrocarbyl radical. Where cyclic, the alkyl group is preferably C₃ to C₁₂, more preferably C₅ to C₁₀, more preferably C₅ to C₇. Where acyclic, the alkyl group is preferably C₁ to C₁₆, more preferably C₁ to C₆, more preferably methyl. Reference in the present specification to an alkoxy group means an alkyl-O— group. Reference to alkoyl group means an alkyl-CO— group.

The alkyl groups may be substituted or unsubstituted, preferably unsubstituted. Where substituted, there will generally be 1 to 3 substituents present, preferably 1 substituent. Substituents may include halogen atoms and halomethyl groups such as CF₃ and CCl₃; oxygen containing groups such as oxo, hydroxy, carboxy, carboxyallyl, alkoxy, alkoxy, alkoyl, alkoyloxy, aryloxy, aryloyl and aryloyloxy; nitrogen containing groups such as amino, amido, alkylamino, dialkylamino, cyano, azide, nitrato and nitro; sulphur containing groups such as thiol, alkylthiol, sulphonyl and sulphoxide; heterocyclic groups containing one or more, preferably one, heteroatom, such as thienyl, furanyl, pyrrolyl, imidazolyl, pyrazolyl, thiazolyl, isothiazolyl, oxazolyl pyrrolidinyl, pyrrolinyl, imidazolidinyl, imidazolinyl, pyrazolidinyl, tetrahydrofuranyl, pyranyl, pyronyl, pyridyl, pyrazinyl, pyridazinyl, benzofuranyl, isobenzofuryl, indolyl, oxyindolyl, isoindolyl, indazolyl, indolinyl, 7-azaindolyl, isoindazolyl, benzopyranyl, coumarinyl, isocoumarinyl, quinolyl, isoquinolyl, naphthridinyl, cinnolinyl, quinazolinyl, pyridopyridyl, benzoxazinyl, quinoxadinyl, chromenyl, chromanyl, isochromanyl and carbolinyl; alkyl groups, which may themselves be substituted; and aryl groups, which may themselves be substituted, such as phenyl and substituted phenyl. Alkyl includes substituted and unsubstituted benzyl.

Reference to amino includes substituted or unsubstituted amino.

Reference in the present specification to halogen means a fluorine, chlorine, bromine or iodine radical, preferably fluorine or chlorine radical.

The present invention extends to dimers and higher multimers of the compounds of the present invention; for example dimers of compounds of the present invention linked via R¹ groups (e.g. via an alkylene chain therein).

Particularly preferred compounds according to the present invention comprise:

4-Nitrato-2,2,6,6-tetramethylpiperidinyloxy, free radical (TEMPO-4-mononitrate)

3,4-Dinitrato-2,2,6,6-Tetramethylpiperidinyloxy, free radical (TEMPO-3,4-dimitrate)

3,4,5-Trinitrato-2,2,6,6-Tetramethylpiperidinyloxy, free radical (TEMPO-3,4,5-trinitrate)

4(2,3-Dinitrato-Prop-1-oxy)2,2,6,6-Tetramethyl-piperidinyloxy, free radical (4-(2,3-dinitrato-prop-1-oxy) TEMPO)

1,3-di (4Oxy-TEMPO)-2-Nitrato-Propane 1,4-di (4-Oxy-TEMPO)-2,3-Dinitrato-Butane

3-Nitrato-4-carboxy-2,2,6,6-tetramethylpiperidinyloxy, free radical (TEMPO-4-carboxyl-3-nitrate)

4Nitrato-3-carbamoyl-2,2,5,5-tetramethyl-3-pyrrolidin-1-yloxy, free radical (PROXYL-3-carbamoyl-4-nitrate)

The present invention further extends to methods of synthesising the compounds of the present invention. The compounds of the present invention may be synthesised according to the following generalised reaction schemes. It will be appreciated that te reaction schemes are merely illustrative of generally applicable procedures which may be modified as appropriate to produce the compounds of the present invention. In the following reaction schemes the 2,2,6,6-tetra substitution present in, for example TEMPO compounds is, for simplicity, not shown.
Reaction Scheme 1
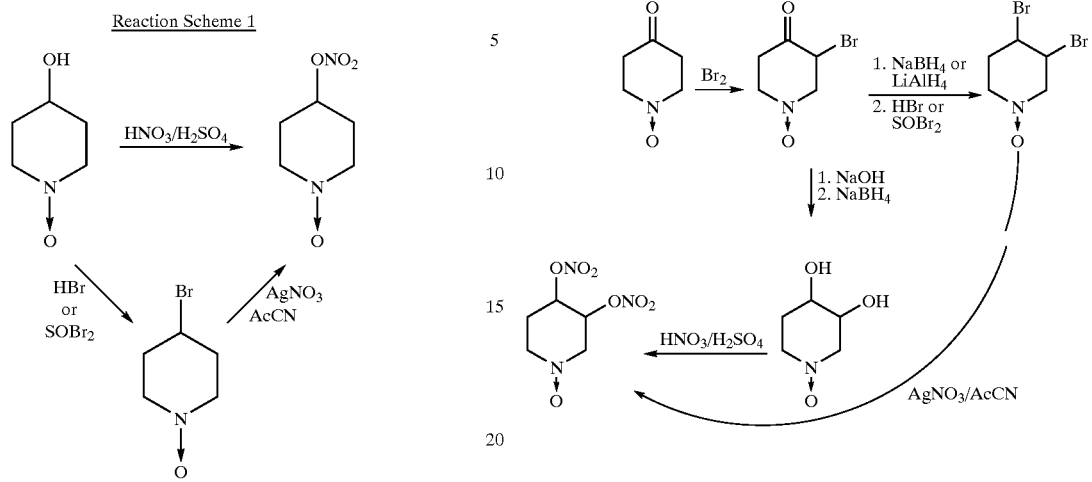
Reaction Scheme 2
Reaction Scheme 3
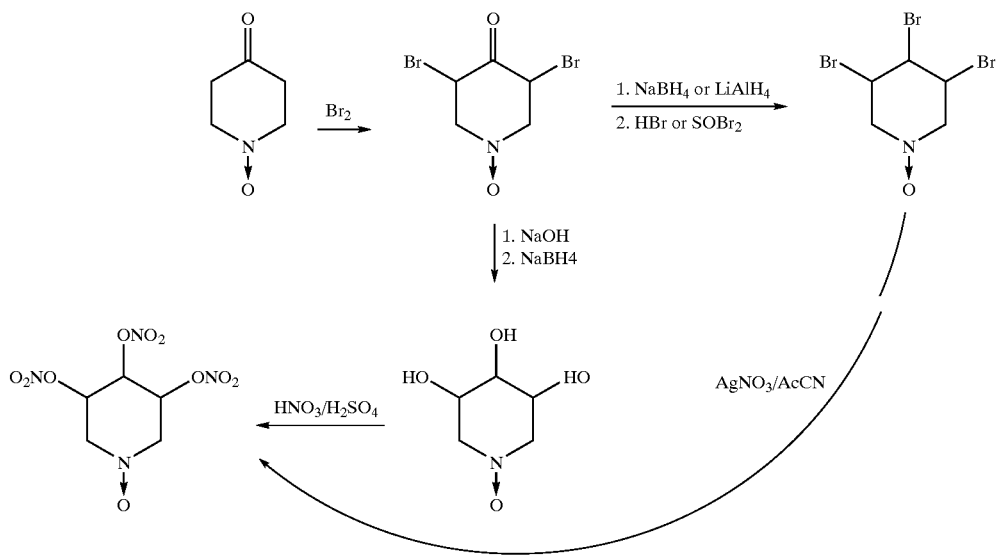
Reaction Scheme 4
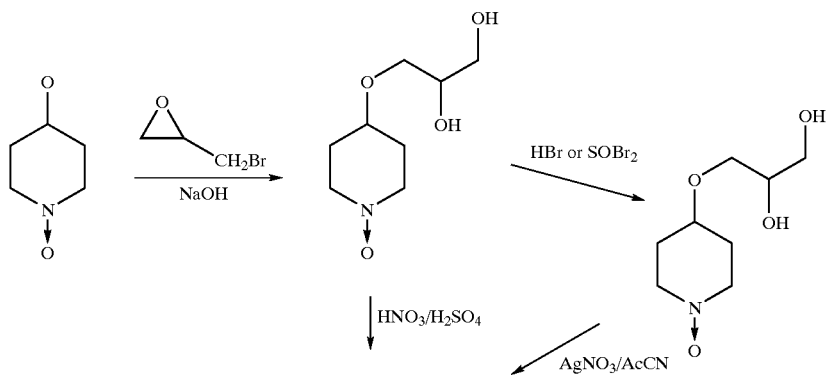

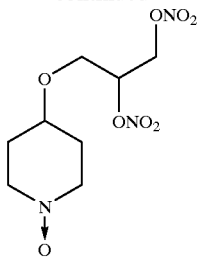
Reaction Scheme 5
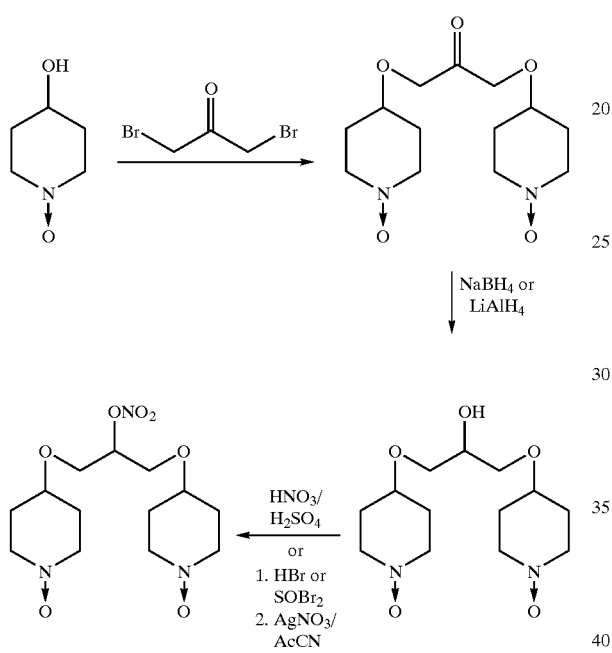
Reaction Scheme 6
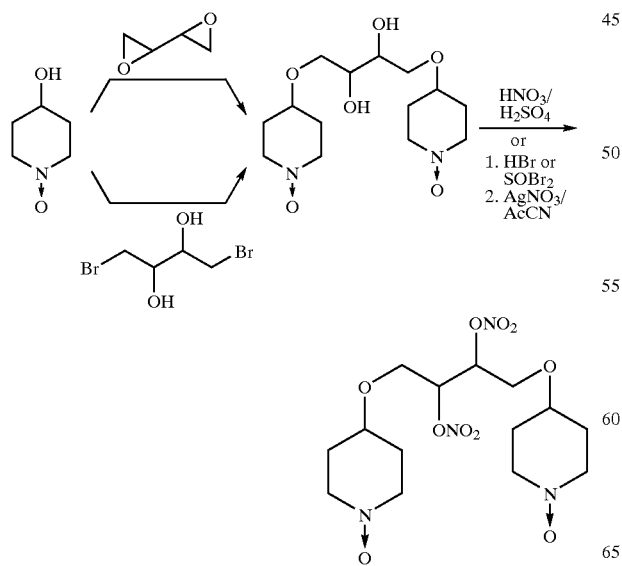
Reaction Scheme 7
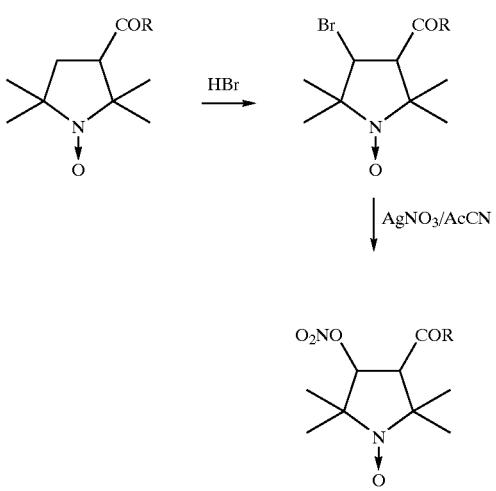
Reaction Scheme 8
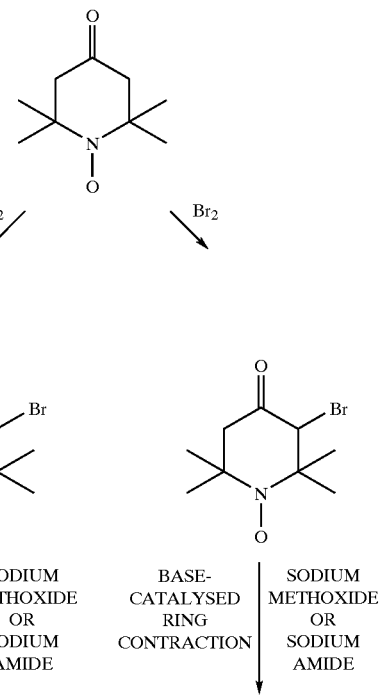

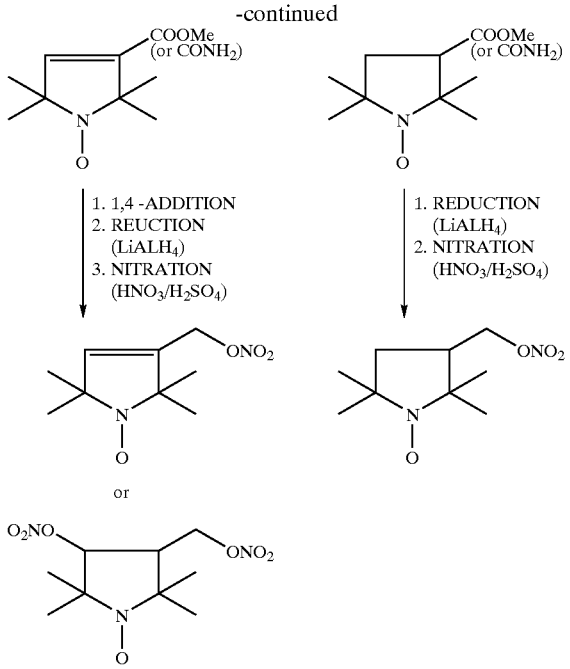

According to a further aspect of the present invention there is provided a compound according to the present invention for use in a method of treatment.

The compounds of the present invention may be employed in the treatment of any condition associated with endothelial dysfunction or oxidative stress including diabetes mellitus, cardiovascular diseases (such as ischaemic heart disease, angina pectoris, myocardial infarction, congestive heart failure, atherosclerosis, hypertension and arrhythmia), asthma, trauma, shock (hypovolumic, neurogenic or septic), neurotoxicity, neurodegenerative and neurological disorders (including Alzheimer and Parkinson's diseases, amyotrophic lateral sclerosis, multiple sclerosis, convulsive (seizure) disorders, AIDS-dementia and disorders which involve processes of learning and memory), disorders of gastric secretions, relaxation and peristalsis of the intestinal tract (including sphincters), drug and disease-induced nephropathies, pathological (premature) and physiological uterine contractions, cellular defense impairment, endothelial dysfunction-induced diseases and insulin-resistance in diabetes, pregnancy-induced hypertension, chemotaxis and phagocytic impairment in immunological disorders, cerebrovascular diseases, aggregation disorders, fertility and reproductive disorders (e.g. penile erection and treatment of male impotence).

According to a further aspect of the present invention there is provided use of a compound according to the present invention for use in the manufacture of a medicament for treating a condition associated with oxidative stress or endothelial dysfunction, preferably diabetes mellitus or cardiovascular disease.

According to a further aspect of the present invention there is provided a method of treating a disease associated with oxidative stress or endothelial dysfunction (such as diabetes mellitus or cardiovascular disease) comprising administering to a patient in need of such treatment an effective dose of a compound of the present invention According to a further aspect of the present invention there is provided a pharmaceutical composition comprising a compound of the present invention in combination with a pharmaceutically acceptable excipient.

Compounds of the present invention may be administered in a form suitable for oral use, for example a tablet, capsule, aqueous or oily solution, suspension or emulsion; for topical use including transmucosal and transdermal use, for example a cream, ointment, gel, aqueous or oil solution or suspension, salve, patch, plaster or as a component of a lubricant for a condom; for nasal use, for an example a snuff, nasal spray or nasal drops; for vaginal or rectal use, for example a suppository; for administration by inhalation, for example a finely divided powder or a liquid aerosol; for sub-lingual or buccal use, for example a tablet or capsule; or for parenteral use (including intravenous, subcutaneous, intramuscular, intravascular or infusion), for example a sterile aqueous or oil solution or suspension, or incorporated in a biodegradable polymer. In general the above compositions may be prepared in a conventional manner using convention excipients, using standard techniques well known to those skilled in the art of pharmacy. Preferably, the compound is administered orally or topically.

For oral administration, the compounds of the invention will generally be provided in the form of tablets or capsules or as an aqueous solution or suspension.

Tablets for oral use may include the active ingredient mixed with pharmaceutically acceptable excipients such as inert diluents, disintegrating agents, binding agents, lubricating agents, sweetening agents, flavouring agents, colouring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

Capsules for oral use include hard gelatin capsules in which the active ingredient is mixed with a solid diluent, and soft gelatin capsules wherein the active ingredient is mixed with water or an oil such as peanut oil, liquid paraffin or olive oil.

For intramuscular, intraperitoneal, subcutaneous and intravenous use, the compounds of the invention will generally be provided in sterile aqueous solutions or suspensions, buffered to an appropriate pH and isotonicity. Suitable aqueous vehicles include Ringer's solution and isotonic sodium chloride. Aqueous suspensions according to the invention may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate. The compounds of the invention may also be provided in a biodegradable polymer, for example for use in conjunction with stints in angioplasty (e.g. adsorbed on a stent or applied directly to the site of the procedure for slow release of the active agent).

It will be appreciated that the dosage levels used may vary over quite a wide range depending upon the compound used, the severity of the symptoms exhibited by the patient and the patient's body weight. Without limitation to the present invention, typical dosages for example for the treatment of angina may be of the order of 1 to 100 mg, preferably 5 to 40 mg, given two or three times daily or 1 to 200 mg, preferably 20 to 50 mg, in sustained release formulations given once or twice daily. Typical dosages for example for acute myocardial infarction may be of the order of 0.1 to 10 mg, preferably 1 to 2 mg, sublingually; 0.5 to 50 mg, preferably 5 to 10 mg, orally; or 1 to 100 micrograms, preferably 10 to 20 micrograms, per minute intravenously.

BRIEF DESCRIPTION OF DRAWINGS.

The invention will now be described with reference to the figures in which.

Figure 1:
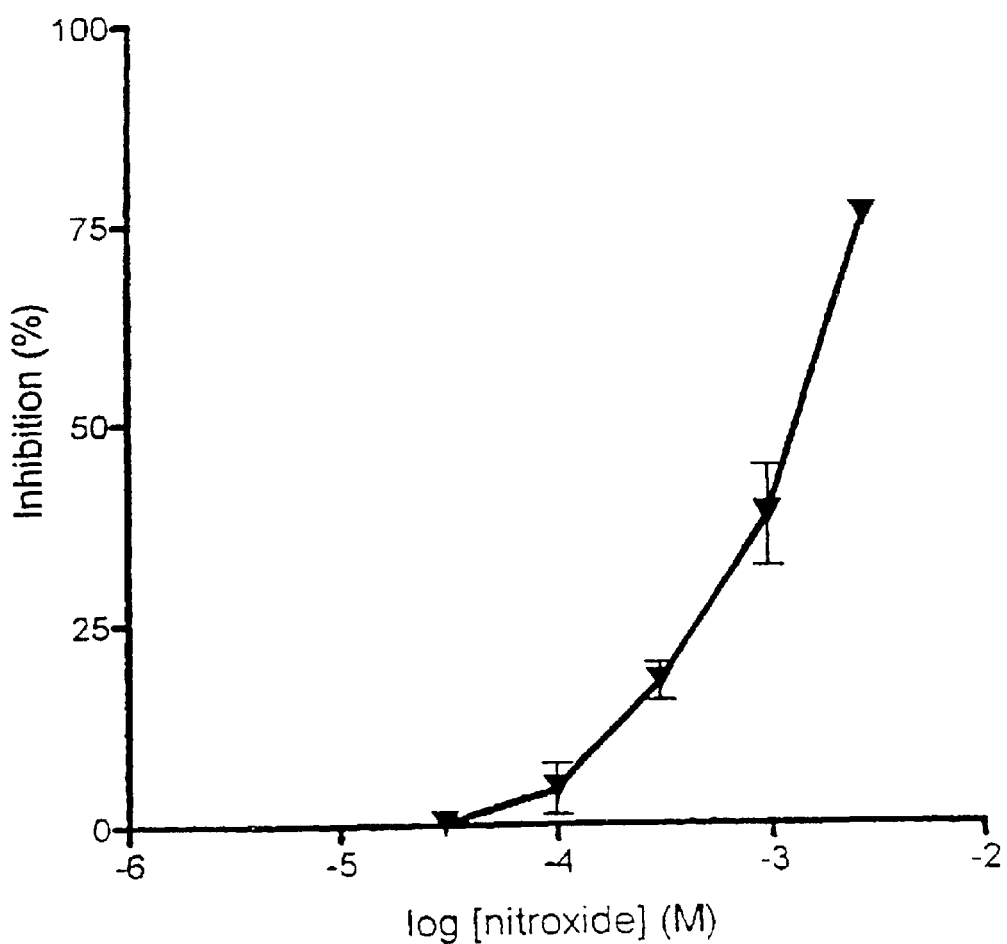
FIG. 1 illustrates inhibition by TEMPO-4-mononitrate of reduction of ferricytochrome C by a xanthine oxidase/hypoxanthine superoxide anion generating system in vitro. Values are mean±s.e.m.

It will be appreciated that the invention is described by way of example only, and that modifications of detail may be made without departing from the scope of the present invention.

EXPERIMENTAL

Synthesis of Compounds

4-Nitrato-2,2.6,6-tetramethylpiperidinyloxy, free radical (TEMPO-4-mononitrate)—(Reaction Scheme 1)

The title compound was prepared by nitration of commercially available 4-hydroxy-TEMPO. 4-Hydroxy-TEMPO (Aldrich Chemical Co.) (20 mmol) was added portionwise to a cooled (0–5° C.) mixture of filming nitric acid (3 ml) and concentrated sulphuric acid (3 ml). After addition was complete, the mixture was brought to room temperature and stirred vigorously for a further 15 minutes. The mixture was added continuously and dropwise to a cooled (5° C.) mixture of diethylether:acetonitrile:water (150 ml:50 ml:25 ml) with vigorous stirring. Sodium chloride (5 g) was added to facilitate separation of the organic layer, which was then evaporated to dryness under reduced pressure. The residue was dissolved in diethyl ether (50 ml) and washed twice with ice-water (20 ml) and once with 2% aq. potassium carbonate (20 ml) before being dried (MgSO4) and evaporated to dryness.

Alternatively, nitration of 4-hydroxy-TEMPO (and nitration of all other hydroxy precursors described by this invention) can be easily achieved by direct exposure of the compound to the gaseous nitrating agent dinitrogen tetroxide ($N_2O_4$). Here, $N_2O_4$ (1.25 equivalents) was introduced to the desired weight into a tarred, precooled (−20° C.) round-bottom flask containing 50 ml of dry tetrahydrofurane-hexane mixture (1:1). 4-Hydroxy-TEMPO (1 equivalent) dissolved in dry tetrahydrofurane (25 ml, −20° C.) was added dropwise into the nitrating solution with stirring. The reaction temperature was maintained below −10° C. during the entire addition period, after which it was left to rise to room temperature within 1 hr. Nitrogen gas was bubbled into the reaction mixture until no more red gas is seen to exit in the upper part of the flask. The organic solvents were evaporated to near dryness and the residue dissolved in methyl tert-butyl ether (100 ml), washed once with water (50 ml) and twice with 50 ml ice-cold 2% sodium bicarbonate solution. The ether was separated, dried ($MgSO_4$) and evaporated to dryness.

The red residue was purified by column chromatography using silica gel (60) and eluted with diethyl ether: petroleum ether (20:80) to furnish the title compound in 90–95% yield. The identity of the product was confirmed by NMR and ESR spectroscopy and by TLC analysis by reaction with diphenylamine, which after heating to 80° C. for 1 minute, gives a deep green colour typical of nitrated nitroxides.

Alternatively, the title compound was prepared by dissolving 3.44 g (20 mmol) of 4-hydroxy-TEMPO in 50 ml of dichloromethane. The mixture was cooled on ice bath and 6 ml of thionyl bromide in 25 ml of dichloromethane was added dropwise during 30 min. After completion the reaction was stirred for an additional 3 hours during which it reached room temperature. The solvent was washed successively with water (75 ml) and 10% sodium carbonate solution (75 ml), dried ($MgSO_4$) and evaporated to dryness. The residue was chromatographed on silica gel and eluted with petroleum ether: dichloromethane (80:20) to furnish 4.71 g (94%) of pure 4-bromo-TEMPO. The product was dissolved in 50 ml of acetonitrile containing 4.25 g (25 mmol) of argentum nitrate. The reaction mixture was heated at 60° C. for 4 hours. The precipitate was removed by filtration and washed with 30 ml of cold acetonitrile. The combined filtrate was removed to dryness under reduced pressure and separated by chromatography as described above to furnish 4.2 g (87%) of the title compound.

The following compounds were prepared using similar procedures and in accordance with the Reaction Schemes set out above:

3,4-Dinitrato-2,2,6,6-Tetramethylpiperidinyloxy, free radical (TEMPO-3,4-dinitrate)

3,4,5-Trinitrato-2,2,6,6-Tetramethylpiperidinyloxy, free radical (TEMPO-3,4,5-trinitrate)

4-(2,3-Dinitrato-Prop-1-oxy)-2,2,6,6-Tetramethyl-piperidinyloxy, free radical (4-(2,3-dinitrato-prop-l-oxy) TEMPO)

1,3-di (4-Oxy-TEMPO)-2-Nitrato-Propane 1,4-di (4-Oxy-TEMPO)-2,3-Dinitrato-Butane 3-Nitrato-4-carboxyl-2,2,6,6-tetramethylpiperidinyloxy, free radical (TEMPO-4-carboxyl-3-nitrate)

3,4-Dinitrato-2,2,6,6-tetramethylpiperidinyloxy, free radical (TEMPO-3,4-dinitrate)—Reaction Scheme 2)

To 4.26 g (25 mmol) of 4-oxo-2,2,6,6-tetramethyl-1-piperidinyloxy, free radical (4-oxo-TEMPO, Aldrich Chemical Co.) dissolved in 50 ml of carbon tetrachloride ($CCL_4$) there was added portion wise 4.895 g (27.5 mmol) of dried, fine powder of N-bromosuccinimide over 25 min with stirring. The reaction was left overnight and filtered. The precipitate was washed with 20 ml of $CCl_4$ and the combined filtrate evaporated to dryness under reduced pressure. The red oil residue (which solidifies to a waxy product upon standing for one day) was chromatographed on silica gel and eluted with chloroform:hexane (60:40) to furnish 5.42 g (87%) of 3-bromo-4-oxo-TEMPO. The product was dissolved in 50 ml of dry diethyl ether and added in one portion to ice-cold 25 ml of 1.0M solution of lithium aluminum hydride in diethyl ether. After stirring for 30 min on ice bath, 25 ml of methanol was added dropwise to destroy excess hydride.

The solvent was filtered and evaporated to dryness. The crude residue was dissolved in dichloromethane (50 ml) and treated for 5 hours with thionyl bromide (6 ml) at room temperature. The reaction mixture was washed twice with equal volumes of water and twice with 5% sodium carbonate solution and organic phase separated and dried on magnesium sulfate. After removing the solvent under reduced pressure, the desired dibromo derivative was isolated by column chromatography (silica gel 60) after elution with petroleum ether. The red oily product was dissolved in 50 ml of acetonitrile containing 30 mmol argentum nitrate and nitration and separation of the desired dinitrated derivative performed as described above for the mononitrated TEMPO. 3,4,5-Trinitrato-2,2,6,6-tetramethylpiperidinyloxy, free radical (TEMPO-3,4,5-trinitrate)—(Reaction Scheme 3)

To 4.26 g (25 mmol) of 4-oxo-2,2,6,6-tetramethyl-1-piperidinyloxy, free radical (4oxo-TEMPO, Aldrich Chemical Co.) dissolved in 150 ml of carbon tetrachloride ($CCl_4$) there was added portion wise 98 g (55 mmol) of dried, fine powder of N-bromosuccinimide over 25 min with stirring. The reaction was left overnight and filtered. The precipitate was washed with 25 ml of $CCl_4$ and the combined filtrate evaporated to dryness under reduced pressure. The red oil residue was chromatographed on silica gel and eluted with chloroform:hexane (30:70) to furnish 6.75 g (82%) of 3,5-dibromo-4-oxo-TEMPO. The product was dissolved in 100 ml of dry diethyl ether and added in one portion to ice-cold 50 ml of 1.0M solution of lithium aluminum hydride in diethyl ether. After stirring for 20 min on ice bath, 25 ml of methanol was added dropwise to destroy excess hydride.

The solvent was filtered and evaporated to dryness. The crude reside was dissolved in dichloromethane (50 ml) and treated for 5 hours with thionyl bromide (6 ml) at room temperature. The reaction mixture was washed twice with equal volumes of water and twice with 5% sodium carbonate solution and organic phase separated and dried on magnesium sulfate. After removing the solvent under reduced pressure, the desired tribromo derivative was isolated by column chromatography (silica gel 60) after elution with heptane. The red oily product was dissolved in 150 ml of acetonitrile containing 0.1 M argentum nitrate and nitration and separation of the desired dinitrated derivative performed as described above for the mono and dinitrated TEMPO. 4-(2,3-Dinitrato-prop-1-oxy)-2,2,6,6-tetramethylpiperidinyloxy, free radical (4-[2,3-dinitrato-prop-1-oxy]-TEMPO)—(Reaction Scheme 4)

4.3g of 4-hydroxy-TEMPO (25 mmol) was dissolved in 50 of dry tetrahydrofuran (THF) and cooled on ice bath. 0.66 g (27.5 mmol) of metal sodium was added in one portion and the reaction mixture stirred vigorously for 40 min. 25 ml of THF containing 3.76 g (27.5 mmol) of eipibromohydrin was added dropwise with stirring at room temperature for one hour. The reaction mixture was evaporated to dryness and residue treated with 20% sodium hydroxide solution for 3 hours at 55° C. After cooling, the reaction mixture was extracted 3 times with 50 ml each of ethyl acetate. The organic layer was separated and the combined extracts dried and evaporated to dryness. The viscous oily residue was added to a cooled (0° C.) mixture of fuming nitric acid and sulfuric acid (3.7 ml each) and stirred for 30 min. The reaction mixture was poured in 1 ml portions into a 300 ml of cold water: acetonitrile:diethyl ether mixture (10:20:70) and stirred for 10 min while nitrogen gas was bubbled into the stirred solution. The organic phase was separated, washed with water and 5% sodium carbonate solution, dried over magnesium sulfate and evaporated to dryness. The reddish oily residue was separated over silica gel and eluted with chloroform to yield 5.1 g (61% based on 4-hydroxy-TEMPO) of the desired product 4-(2.3-Dinitrato-prop-1-oxy)-2,2,6,6-tetramethylpiperidinyloxy, free radial (4-[2,3-dinitrato-prop-1-oxy]-TEMPO).

1,3-Di-(4-oxy-TEMPO)-2-nitratopropane—(Reaction Scheme 5)

8.6 g (50 mmol) of 4-hydroxy-TEMPO were dissolved in 80 ml of dry tetrahydrofuran (THF) and cooled on ice bath. 1.44 g (60 mmol) of metal sodium was added in one portion and the reaction mixture stirred vigorously for 40 min. 25 ml of THF containing 5.4 g (25 mmol) of dibromoacetone was added dropwise with stirring at room temperature for one hour. The reaction mixture was cooled on ice-water bath and 30 ml of 1.0 M solution of lithium aluminum hydride in diethyl ether was added in one portion. After stirring for 20 min on ice bath, 25 ml of methanol was added dropwise to destroy excess hydride. The solvent was filtered and evaporated to dryness. The viscous oily residue was added to a cooled (0° C.) mixture of fuming nitric acid and sulfuric acid (3.7 ml each) and stirred for 30 min. The reaction mixture was poured in 1 ml portions into a 300 ml of cold water: acetonitrile:diethyl ether mixture (10:20:70) and stirred for 10 min while nitrogen gas was bubbled into the stirred solution. The organic phase was separated, washed with water and 5% sodium carbonate solution, dried over magnesium sulfate and evaporated to dryness. The reddish oily residue was separated over silica gel and eluted with dichloromethane:diethyl ether (80:20) to yield 6.45 g (57% based on 4-hydroxy-TEMPO) of the desired product 1,3-Di-(4-oxy-TEMPO)-2-nitratopropane.

1,4-Di-(4-oxo-TEMPO)-2.3-dinitratobutane—(Reaction Scheme 6)

8.6 g (50 mmol) of 4-hydroxy-TEMPO were dissolved in 80 ml of dry tetrahydrofuran (THF) and cooled on ice bath. 1.44 g (60 mmol) of metal sodium was added in one portion and the reaction mixture stirred vigorously for 40 min 25 ml of THF containing 2.15 g (25 mmol) of (±)-1,3-butadiene diepoxide was added dropwise with stirring at room temperature for five hours. The reaction mixture was filtered and evaporated to dryness. The viscous oily residue was added to a cooled (0° C.) mixture of fuming nitric acid and sulfinic acid (5.8 ml each) and stirred for 30 min. The reaction mixture was poured in 1 ml portions into a 300 ml of cold water:acetonitrile:diethyl ether mixture (10:20:70) and stirred for 10 min while nitrogen gas was bubbled into the stirred solution. The organic phase was separated, washed with water and 5% sodium carbonate solution, dried over magnesium sulfate and evaporated to dryness. The reddish oily residue was separated over silica gel and eluted with dichloromethane:diethyl ether (60:40) to yield 5.59 g (43% based on 4-hydroxy-TEMPO) of the desired product 1,4-Di-(4-oxo-TEMPO)-2.3-dinitratobutane.

4-Nitrato-3-carbamoyl-2,2,5,5-tetramethyl-3-pyrrolidin-1-yloxy, free radical (PROXYL-3-carbamoyl-4-nitrate)—(Reaction Scheme 7)

3.6 g (20 mmol) of 3-carbamoyl-2,2,5,5-tetramethyl-3-pyrrolin-1-yloxy, free radical commercially available from Aldrich Chemical Co. was added portion wise to 6 ml of cool concentrated hydrobromic acid solution containing 50 mg of 1,1'-azobis (cyclohexanecarbonitrile) and stirred overnight. The resulting solution was diluted with 14 ml of ice cold water and extracted 5 times each of 50 ml of ether. The combined ether extracts was washed twice with water and twice with 30 ml each of 5% sodium carbonate solution. The organic solvent was dried (sodium sulfate) and evaporated to dryness. The resulting crude 4bromo-3-carboxy derivative was dissolved in 50 ml of acetonitrile, 6 g of argentum nitrate were added and the solution refluxed for 2 hrs. After cooling to room temperature, the inorganic salts were removed by filtration and the organic solvent removed. The residue was triturated with a mixture of hexane-ether solution (1:1) and the solvent removed The residue was then separated by flash chromatography (dichloromethane:ethyl acetate 4:1) to give the pure title compound.

3-Nitratomethyl-2,2,5,5-tetramethylpyrrolidinyloxy, free radical (3-nitratomethyl-PROXYL)

To 4.26 g (25 mmol) of 4-oxo-2,2,6,6-tetramethyl-1-piperidinyloxy, free radical (4-oxo-TEMPO) dissolved in 50 ml of carbon tetrachloride ($CCl_4$) there was added portion wise 4.895 g (27.5 mmol) of dried, fine powder of N-bromosuccinimide over 25 min with stirring. The reaction was left overnight and filtered. The precipitate was washed with 20 ml of $CCl_4$ and the combined filtrate evaporated to dryness under reduced pressure. The red oil residue (which solidifies to a waxy product upon standing for one day) was chromatographed on silica gel and eluted with chloroform-:hexane (60:40) to furnish 5.42 g (87%) of 3-bromo-4-oxo-TEMPO. The product was dissolved in 20 ml of methanol and added dropwise to 30 ml of ice-cold, freshly prepared solution of sodium methoxide (60 mmol). After addition is complete, the reaction mixture is stirred at room temperature for 5 hours at the end of which the reaction is brought to reflux for 30 min. After cooling, the solvent was filtered and evaporated to dryness under reduced pressure. The residue was dissolved in 50 ml of dry diethyl ether and added dropwise to 30 ml of 1.0 M solution of lithium aluminum hydride in diethyl ether. After stirring for 20 min on ice bath, 25 ml of methanol was added dropwise to destroy excess hydride. The solvent was filtered and evaporated to dryness. The viscous oily residue was added to a cooled (0° C.) mixture of fuming nitric acid and sulfric acid (3.7 ml each) and stirred for 30 min. The reaction mixture was poured in 1 ml portions into a 300 ml of cold water:acetonitrile:diethyl ether mixture (10:20:70) and stirred for 10 min while nitrogen gas is bubbled into the stirred solution. The organic phase was separated, washed with water and 5% sodium carbonate solution, dried over magnesium sulfate and evaporated to dryness. The yellow-orange oily residue was separated over silica gel and eluted with dichloromethane-:hexane (80:20) to yield the title compound 3-nitratomethyl-2,2,5,5-tetramethylpyrrolidinyloxy, free radical (3-nitratomethyl-PROXYL) in 63% yield.

Biological Testing

Assessment of superoxide scavenging activity in vitro

The superoxide scavenging activity of TEMPO-4-mononitrate (0.003–3 mM) and reference compound superoxide dismutase (SOD, 200 U/ml), were determined using a photometric microassay in vitro (Laight et al., Environ. J. Toxicol. Pharmracol., 3, 65–68, 1997) developed from the assay of McCord & Fridovich (J. Biol. Chem., 244, 6059–55, 1969). The assay mixture consisted of (final concentration): 50 $\mu$l ferricytochrome c (100 $\mu$M); 10 $\mu$l xanthine oxidase (20 mU/ml); 20 $\mu$l hypoxanthine (100 $\mu$M); and 20 $\mu$l sample dissolved in isotonic phosphate (10 mM)-buffered saline (PBS, pH 7.4) to make a total volume of 100 $\mu$l in a 96-well plate. The reaction was conducted at room temperature and initiated by the addition of hypoxanthine. The increase in optical density (OD) at 500 nm was measured over a 3 min period of 30 s intervals and initial reaction rates determined at least in triplicate.

There was a linear relationship between the initial reaction rate and the concentration of xanthine oxidase (5–20 mU/ml) (r=0.9982, P<0.002, n=4). Blank controls lacking either enzyme or substrate showed no activity. Xanthine oxidase at 20 mU/rml, which provided an initial reaction rate of 28.3±1.7 mOD/min (n=4), was adopted for subsequent inhibition studies (see McCord & Fridovich, 1969). The initial reaction rate was depressed by SOD (200 U/ml) by 95.3±1.1% (n=4, P<0.01) and by TEMPO-4-mononitrate (see FIG. 1). TEMPO-4-mononitrate exhibited a $pIC_{50}$ value of 2.89±0.03 (n=5,p<0.001).

Vasorelaxation and Tolerance-Inducing Properties

Materials: Male Sprague-Dawley rats (250–300 g) were purchased from the Animal Care Facility of the Hebrew University and used in the rat aortic rings (RARs) relaxation studies in vitro and the blood pressure monitoring and cGMP studies in vivo.

Figure 2:
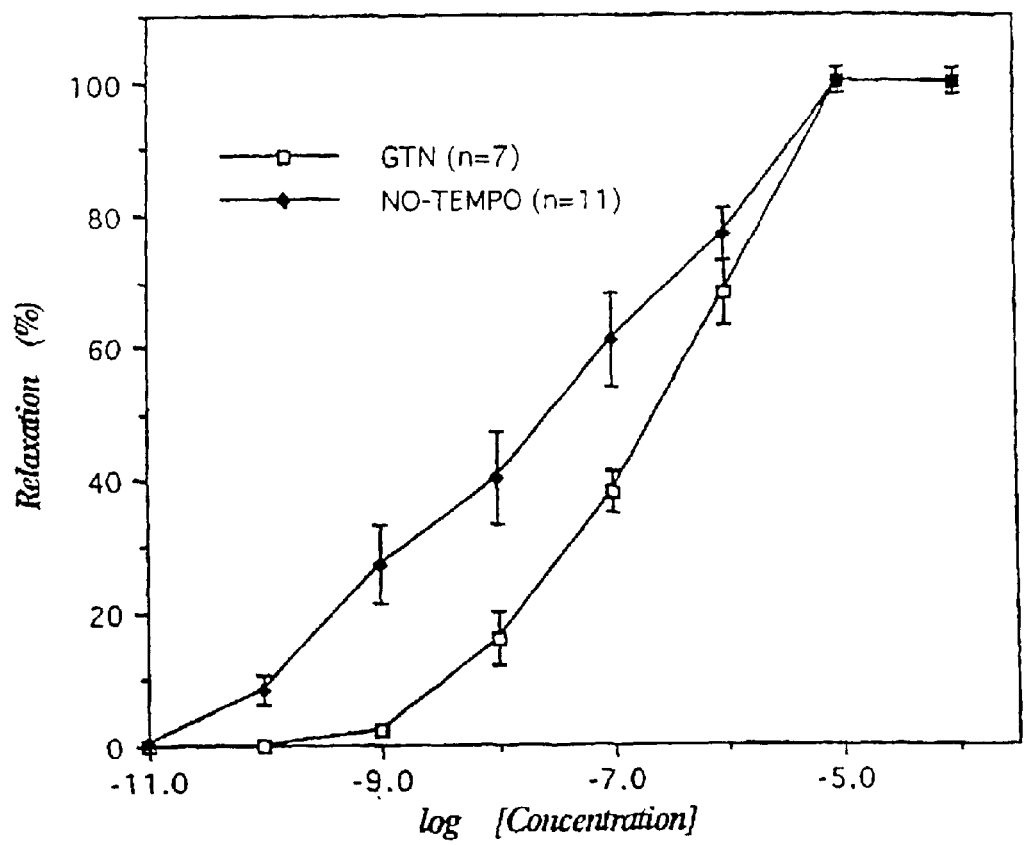
FIG. 2 illustrates relaxation response curves of control RARs to GTN and NO-TEMPO.
Figure 3:
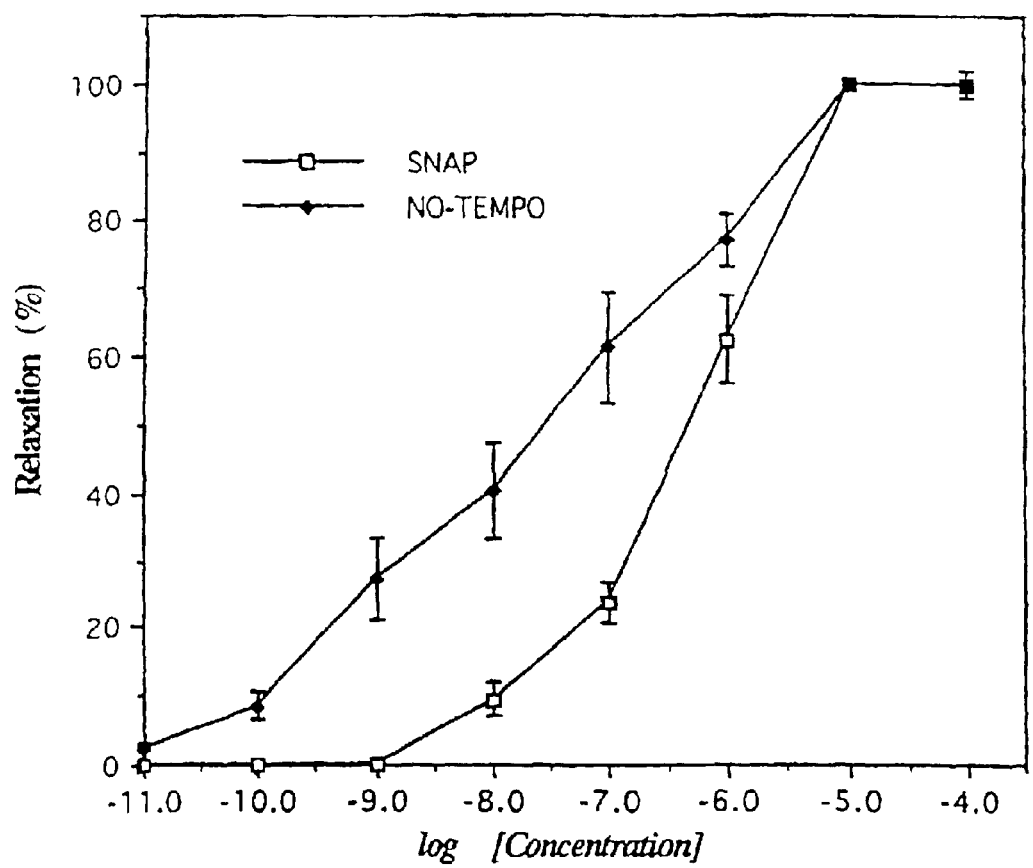
FIG. 3 illustrates relaxation response curves of control RARs to SNAP (n=8) and NO-TEMPO (n=11)

In vitro vasorelaxation: Thoracic aortae were removed following anesthesia with intraperitoneal injection of ketamine and xylazine (50 and 10 mg/kg, respectively). The paraadventetial tissue surrounding the vessel was carefully removed. Aortae were cut into rings of 4–5 mm and mounted onto the tissue path. The path buffer (Krebs-bicarbonate) was constantly gassed with carbogen and maintained at 37° C. The rings were preloaded under 2 g tension and equilibrated for 90 min with buffer changed every 15 min. After stabilization, the rings were contracted with epinephrine (1 $\mu$M). Commulative Concentration-Response Curves (CCRC) were constructed for NO-TEMPO, glyceryl trinitrate (GTN) and S-nitroso-N-acetylpenicillamine (SNAP). FIGS. 2 and 3 represent the vaso-relaxant effect of NO-TEMPO as compared to the conventional NO-donors GTN and SNAP. These figures demonstrate the superiority of NO-TEMPO to both of these NO-donors.

Figure 4:
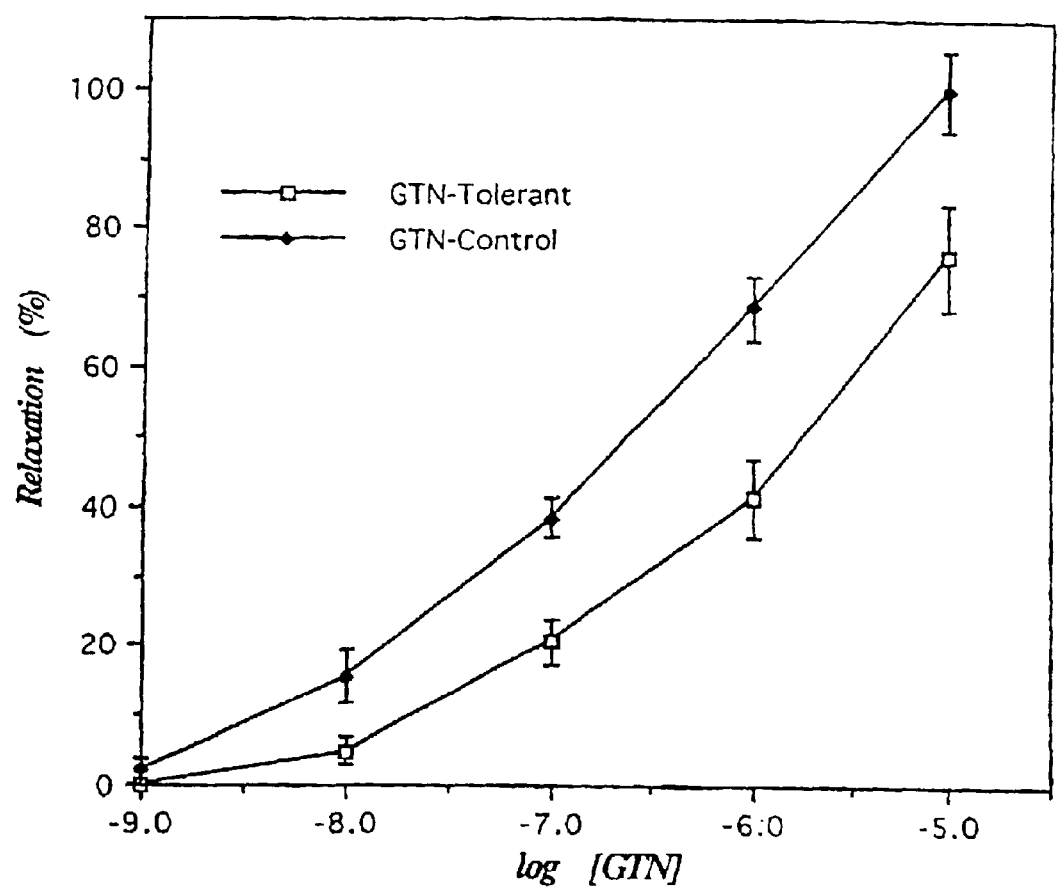
FIG. 4 illustrates relaxation response curves to GTN of control and GTN-tolerant RARs.
Figure 5:
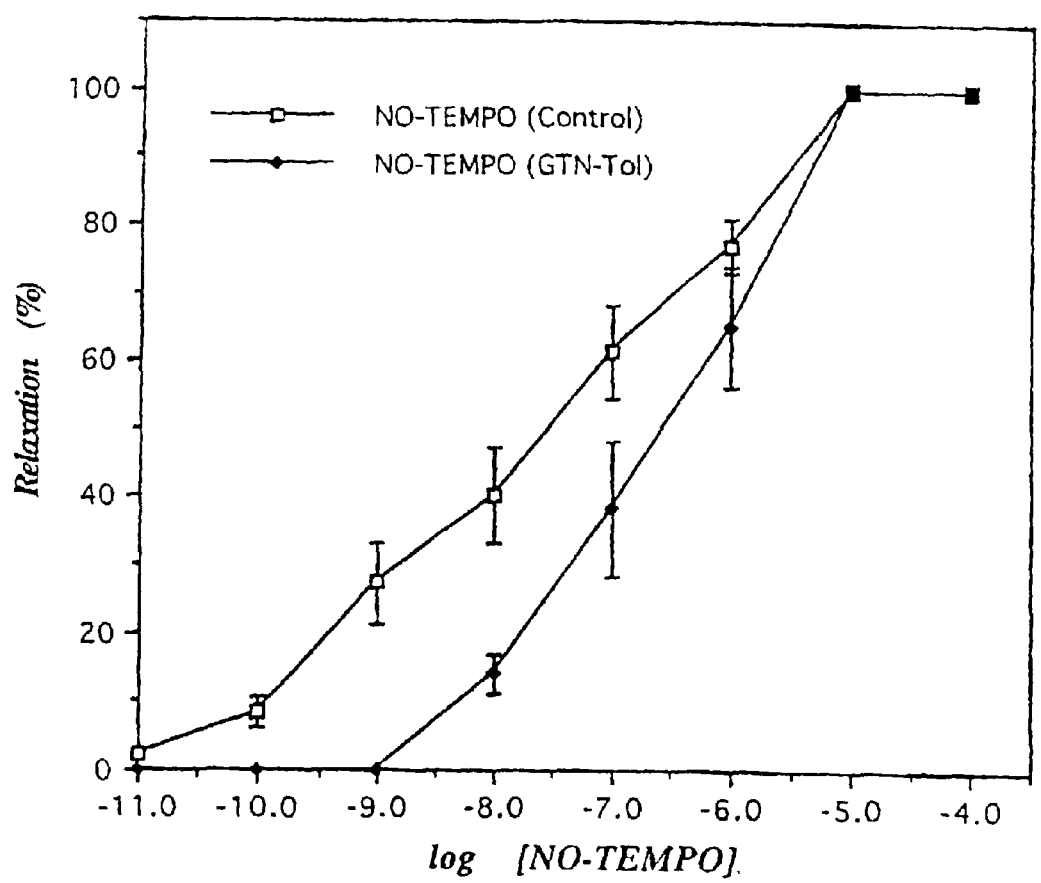
FIG. 5 illustrates relaxation response curves to NO-TEMPO of control (n=11) and GTN tolerant (n=7) RARs.
Figure 6:
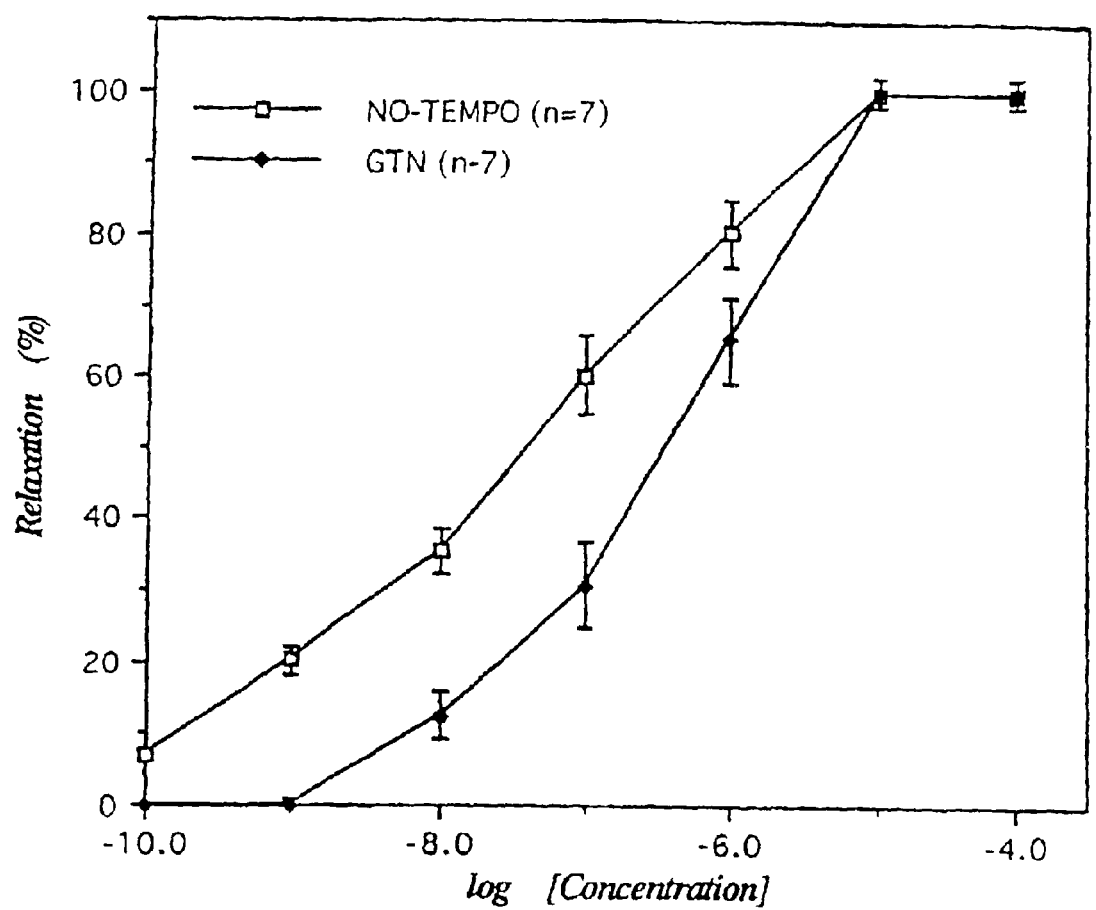
FIG. 6 illustrates relaxation response curves of NO-TEMPO-pretreated RARs (0.44 mM of NO-TEMPO) to GTN and NO-TEMPO.
Figure 7:
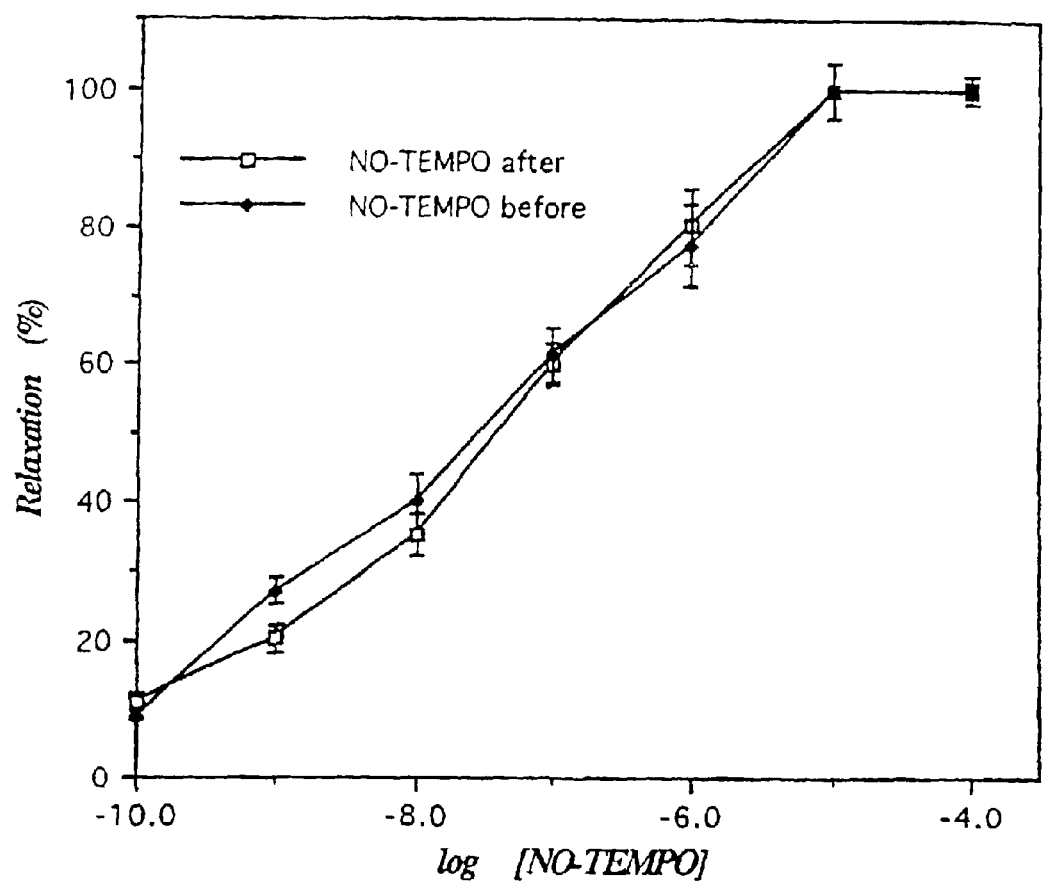
FIGS. 7 illustrates relaxation response curves to NO-TEMPO before and after pretreatment of RARs with 0.44 mM of NO-TEMPO.
Figure 8:
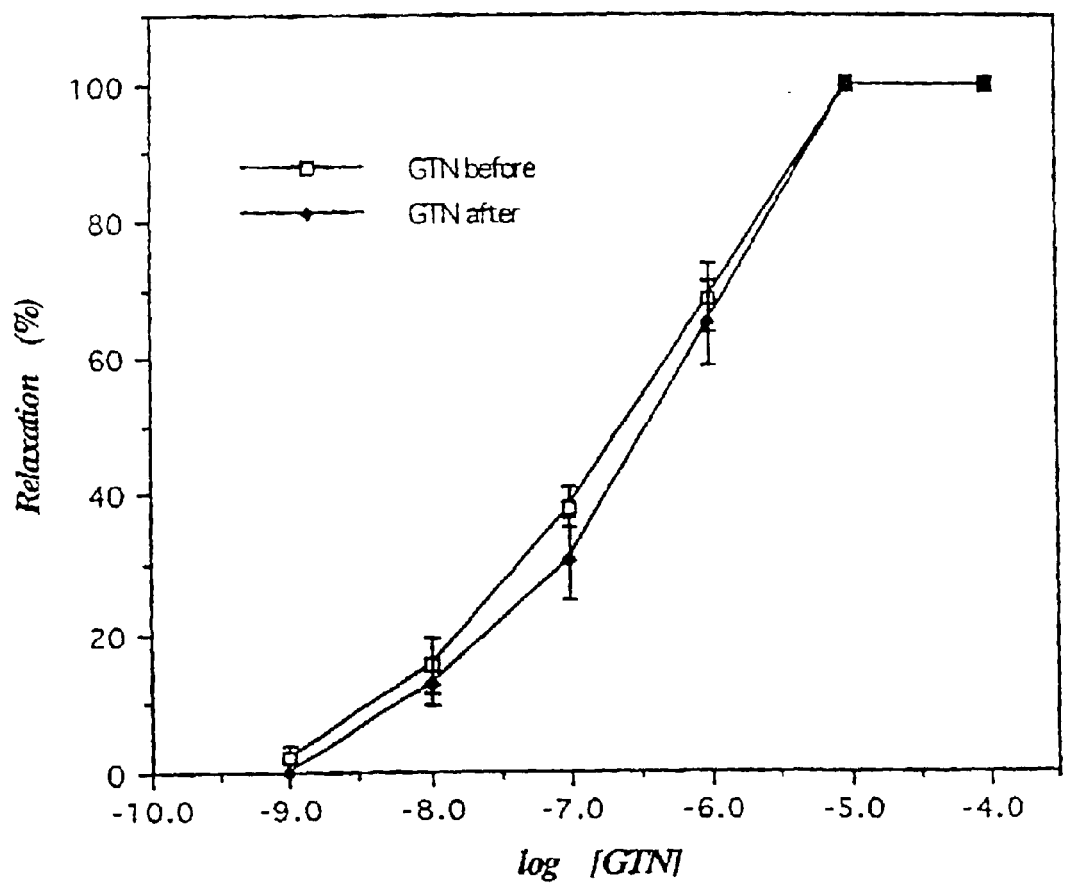
FIG. 8 illustrates relaxation response curves of RARs (n=8) to GTN before and after pretreatment with 0.44 mM of NO-TEMPO.

In vitro induction of GTN tolerance: Aortic rings were treated as for the control studies except that rings were exposed to 0.44 mM GTN for 1 hr. At the end of the tolerance induction period, rings were washed every 15 min for the following hour. Attempted induction of tolerance to NO-TEMPO was performed under the same conditions as for GTN with rings exposed to 0.44 mM solution of NO-TEMPO. CCRC were constructed for NO-TEMPO and GTN. FIG. 4 shows the vaso-relaxant effect of GTN on rings before and after exposure to 0.44 mM of the drug and it clearly demonstrates the development of GTN tolerance under these conditions. This tolerance is also crossed to NO-TEMPO as is obvious from FIG. 5, where a significant difference between the effects of NO-TEMPO on rings before and after pre-treatment with GTN exists. However, when the vaso-relaxant activity of NO-TEMPO and GTN were examined using NO-TEMPO-pre-treated RARs, no significant differences between the potencies of these drugs were obtained between control RARs FIG. 2) and NO-TEMPO-pretreated RARs (FIG. 6). This observation demonstrates that, under the condition applied, tolerance to NO-TEMPO does not develop. This conclusion is further supported by separately evaluating the vaso-relaxant effect of each drug on control and NO-TEMPO-pre-treated RARs. Thus, as is obvious from FIG. 7, no significant difference was observed in the vaso-relaxant potency of NO-TEMPO between control and NO-TEMPO-pre-treated RARs. Similarly, no significant difference exists in the potency of GTN between control and NO-TEMPO-pre-treated RARs (FIG. 8). These results demonstrate that, whereas GTN induces tolerance both to itself and to NO-TEMPO, NO-TEMPO does not induce tolerance neither to itself nor to GTN.

In vivo vasorelaxation and induction of GTN tolerance

Results obtained from evaluating the hypotensive effects of NO-TEMPO in vivo also demonstrated the superiority of this drug to both GTN and SNAP. Moreover, vascular cGMP measurements following in vivo administration of NO-TEMPO showed its superior activity as compared to GTN in control rats and the lack of tolerance induction to its effect in NO-TEMPO pre-treated rats.

In the in vivo experiment, rats were anesthetized with an intraperitoneal injection of a combination of ketamine and xylazine (50 and 10 mg per kg, respectively). A catheter was placed in the right external jugular vein and introduced to the level of right atrium. A second arterial catheter was placed in the left carotid artery and introduced to the level of the ascending aorta. The tip of arterial catheter was connected to a pressure transducer which is connected to another electrical transducer connected to a computerized Experimetria system. Blood-pressure (mean arterial pressure=MAP) was recorded before (basal) and after drug administration. NO-TEMPO was injected through the venous catheter and induced a significant drop in MAP which lasts for 5 to 10 minutes. Values for basal MAP were 130±15 before and 60±10 mm Hg following a 1 mg injection of NO-TEMPO. Unlike with GTN and SNAP, where attenuation to their effect on MAP develops, the hypotensive effect of NO-TEMPO on MAP was consistent and was repeatable following successive administration of NO-TEMPO, which indicated the lack of tolerance development to the drug.

Effect on cGMP and Tolerance to Organic Nitrates

Administration of TEMPO-4-mononitrate resulted in a significant increase in cGMP content of vascular tissue. Although it bears only one nitrate group, the effect of TEMPO-4-mononitrate on vascular cGMP compared well with that of GTN, despite the latter containing 3 such groups when both drugs are administered intravenously in equimolar doses to control rats.

Experiments were performed in anaesthetized rats as above. Following i.v. administration of NO-TEMPO (0.1, 0.2, 0.5 mg etc.,) the thorax was opened and the aorta removed immediately (within thirty seconds from the administration). After standard processing procedures, cGMP content in the vascular tissue was measured by Radioimmunoassay (RIA) using commercially available kits (i.e., Kit 500 TRK from Amersham). Typical basal values of cGMP in aortic tissue were 46±10 versus 197±18 pmole/g tissue obtained following administration of 1 mg of NO-TEMPO (a 4–5-fold increase in vascular cGMP).

When given subcutaneously (30 mg/kg t.i.d for three consecutive days), NO-TEMPO does not induce tolerance either to itself or to GTN, whereas GTN administered in the same route does induce tolerance to itself and to NO-TEMPO.

Conclusion

It is clear that the compounds of the present invention exhibit both superoxide scavenging and vasodilator activity, fulfilling the combined roles of organic nitrate and antioxidant. Moreover, they act as potent superoxide anion scavengers at concentrations which liberate therapeutic amounts of NO. In addition, the compounds of the present invention do not induce tolerance to themselves or conventional organic nitrates. The compounds of the present invention therefore have exceptional therapeutic utility, particularly in conditions with adverse responsiveness to organic nitrates.

What is claimed is:

1. A compound of the formula:

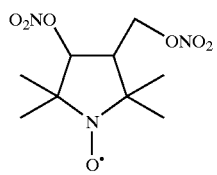

or a pharmaceutically acceptable salt thereof.

2. A composition comprising the compound of claim 1 and a pharmaceutically acceptable excipient.

3. The composition of claim 2, in a form suitable for administration to a patient, wherein the form suitable for administration is selected from the group consisting of a form suitable for topical administration, administration by inhalation, nasal administration, parenteral administration and oral administration.

4. The composition of claim 3, wherein the composition is in a form suitable for topical administration.

5. The composition of claim 4, wherein the composition is in the form of a cream, ointment, gel, aqueous or oil solution or suspension, salve, patch, plaster, lubricant or suppository.

6. The composition of claim 3, wherein composition is in a form suitable for oral administration.

7. The composition of claim 6, wherein the composition is in the form of a tablet, capsule, aqueous or oily solution, suspension or emulsion.

8. The composition of claim 3, wherein the composition is in a form suitable for parenteral administration.

9. A composition comprising the compound of claim 1 and a biodegradable polymer.

10. The composition of claim 9, wherein the polymer is adsorbed on a stent or applied directly to the site of the angioplasty procedure.

11. The composition of claim 9, wherein the composition is formulated for slow release of the compound.

12. A compound of the formula:

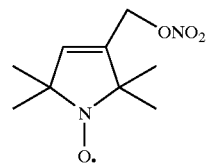

or a pharmaceutically acceptable salt thereof.

13. A composition comprising the compound of claim 12 and a pharmaceutically acceptable excipient.

14. The composition of claim 13, in a form suitable for administration to a patient, wherein the form suitable for administration is selected from the group consisting of a form suitable for topical administration, administration by inhalation, nasal administration, parenteral administration and oral administration.

15. The composition of claim 14, wherein the composition is in a form suitable for topical administration.

16. The composition of claim 15, wherein the composition is in the form of a cream, ointment, gel, aqueous or oil solution or suspension, salve, patch, plaster, lubricant or suppository.

17. The composition of claim 14, wherein composition is in a form suitable for oral administration.

18. The composition of claim 17, wherein the composition is in the form of a tablet, capsule, aqueous or oily solution, suspension or emulsion.

19. The composition of claim 14, wherein the composition is in a form suitable for parenteral administration.

20. A composition comprising the compound of claim 13 and a biodegradable polymer.

21. The composition of claim 20, wherein the polymer is adsorbed on a stent or applied directly to the site of the angioplasty procedure.

22. The composition of claim 20, wherein the composition is formulated for slow release of the compound.

23. A method of treating a condition associated with oxidative stress or endothelial dysfunction comprising administering to a patient in need of such treatment a nitric oxide liberating and a superoxide dismutase mimetic effective amount of a compound of the formula:

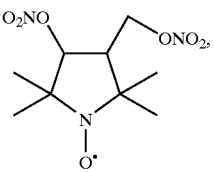 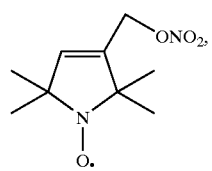

a pharmaceutically acceptable salt thereof or a mixture thereof, such treatment a nitric oxide liberating and a superoxide dismutase mimetic effective amount of a compound of the formula:

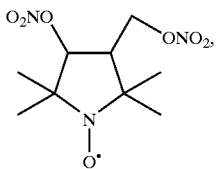 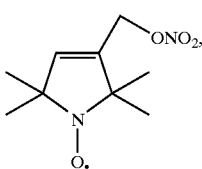

a pharmaceutically acceptable salt thereof or a mixture thereof.

24. The method of claim 23, wherein the condition is a cardiovascular disease.

25. The method of claim 23, wherein the condition is insulin resistance in diabetes.

26. The method of claim 23, wherein the condition is a reproductive disorder selected from the group consisting of penile erection disorder and male impotence.

27. The method of claim 24, wherein the cardiovascular disease is angina pectoris, atherosclerosis, or hypertension.

28. The method of claim 24, wherein the method comprises administering the compound in conjunction with a stent in angioplasty.

29. The method of claim 23, wherein the compound is administered topically, by inhalation, nasally, parenterally or orally.

30. The method of claim 23, wherein the method comprises administering a composition comprising a biodegradable polymer and the compound to the patient.

31. A method of treating a diabetic condition associated with oxidative stress or endothelial dysfunction, comprising administering to a patient in need of
wherein the condition is selected from the group consisting of cardiovascular disease, diabetes, neurodegenerative or neurological disorders, drug and disease-induced nephropathies, and reproductive disorders.

32. A compound having the formula:

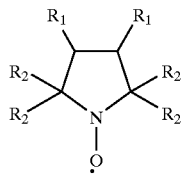

wherein:
each $R^1$ is, independently, hydrogen, alkoyl, alkoxy, carboxy, hydroxy, amino, cyano, nitro, alkyl or a nitric oxide donor group of the formula —X—Y—$ONO_2$,
wherein:
X is O, NH, or S; and
Y is a $C_{1-20}$ alkylene chain, and
wherein at least one $R^1$ is said nitric oxide donor group and
each $R^2$ is alkyl; or
a pharmaceutically acceptable salt thereof.

33. The compound of claim 32, wherein each $R^2$ is methyl.

34. A method of treating a condition associated with oxidative stress or endothelial dysfunction comprising administering to a patient in need of such treatment a nitric oxide liberating and a superoxide dismutase mimetic effective amount of the compound of claim 32,
wherein the condition is selected from the group consisting of cardiovascular disease, diabetes, neurodegenerative or neurological disorders, drug and disease-induced nephropathies, and reproductive disorders.

35. The method of claim 34, wherein the condition is a cardiovascular disease.

36. The method of claim 34, wherein the condition is insulin resistance in diabetes.

37. The method of claim 34, wherein the condition is a reproductive disorder selected from the group consisting of penile erection disorder and male impotence.

38. The method of claim 35, wherein the cardiovascular disease is angina pectoris, atherosclerosis, or hypertension.

39. The method of claim 35, wherein the method comprises administering the compound in conjunction with a stent in angioplasty.

40. The method of claim 34, wherein the compound is administered topically, by inhalation, nasally, parenterally or orally.

41. The method of claim 34, wherein the method comprises administering a composition comprising a biodegradable polymer and the compound to the patient.

42. A method of treating a diabetic condition associated with oxidative stress or endothelial dysfunction, comprising administering to a patient in need of such treatment a nitric oxide liberating and a superoxide dismutase mimetic effective amount of the compound of claim 32.

* * * * *